United States Patent [19]

Averill et al.

[11] Patent Number: 5,089,004

[45] Date of Patent: Feb. 18, 1992

[54] PROSTHETIC IMPLANT PROCEDURE AND FEMORAL BROACH THEREFOR

[75] Inventors: Robert G. Averill, Ringwood; Robert C. Cohen, Denville, both of N.J.

[73] Assignee: Osteonics Corp., Allendale, N.J.

[21] Appl. No.: 145,793

[22] Filed: Jan. 19, 1988

[51] Int. Cl.[5] .................. A61B 17/00; A61F 2/32; A61F 2/36

[52] U.S. Cl. .................... 606/85; 606/89; 623/23

[58] Field of Search .......... 128/92 Y, 92 YZ, 92 YK, 128/92 YV, 92 VT, 92 VD; 623/18, 23; 606/62, 63, 79, 80, 83, 84, 85, 89

[56] References Cited

U.S. PATENT DOCUMENTS

| | | | |
|---|---|---|---|
| 2,719,522 | 10/1955 | Hudack | 623/23 |
| 3,067,740 | 12/1962 | Haboush | 623/23 |
| 4,199,824 | 4/1980 | Niederer | 623/23 |
| 4,352,212 | 10/1982 | Greene et al. | 623/18 |
| 4,530,115 | 7/1985 | Müller et al. | 623/23 |
| 4,551,863 | 11/1985 | Murray | 623/23 |
| 4,608,053 | 8/1986 | Keller | 623/23 |
| 4,642,121 | 2/1987 | Keller | 623/23 |
| 4,645,506 | 2/1987 | Link | 623/23 |
| 4,664,668 | 5/1987 | Beck et al. | 623/23 |
| 4,693,724 | 9/1987 | Rhenter et al. | 623/23 |

*Primary Examiner*—Robert A. Hafer
*Assistant Examiner*—Michael Brown

*Attorney, Agent, or Firm*—Samuelson & Jacob

[57] ABSTRACT

A procedure for contouring the wall of a femoral cavity in a femur for the reception of a femoral stem to be seated within the femoral cavity employs a femoral broach which includes cutting teeth aligned along peripherally spaced apart longitudinal rows extending along a portion of the outer surface of the blade of the broach for forming a multiplicity of alternating longitudinally extending generally parallel grooves and ribs in the wall of the cavity, at least some of the grooves being contiguous with harder portions of the bone of the femur while the ribs are comprised of softer portions of the bone so that completion of the contouring will be signalled by bottoming of the blade of the broach upon the harder portions of the bone and upon implant, the femoral stem will be seated upon the harder portions of bone while the softer portions of bone will be compressed between the femoral stem and the harder portions of bone to accomplish fixation by an interference fit. Upon completion of the contouring of the wall of the cavity, and prior to withdrawal of the blade of the femoral broach, the seated blade of the broach serves as a true gauge of the subsequent location of the femoral stem relative to the femur. A vented, interchangeable distal tip on the blade of the broach pilots the broach for precise alignment of the blade during the contouring procedure.

21 Claims, 2 Drawing Sheets

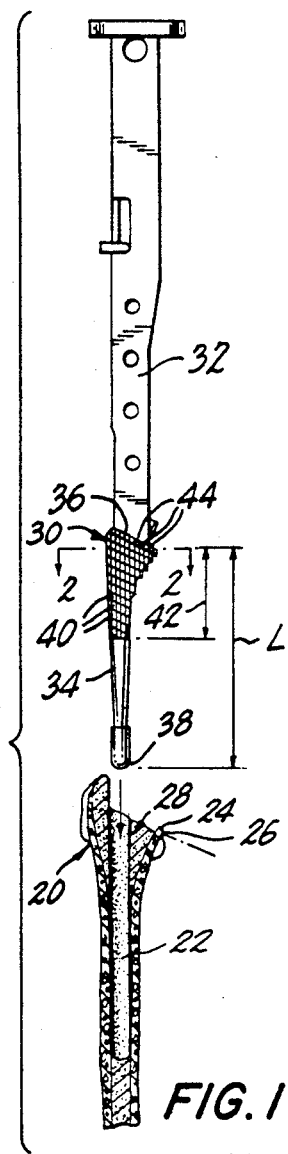
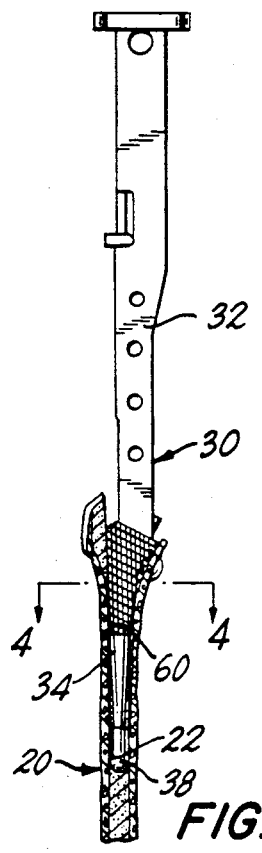
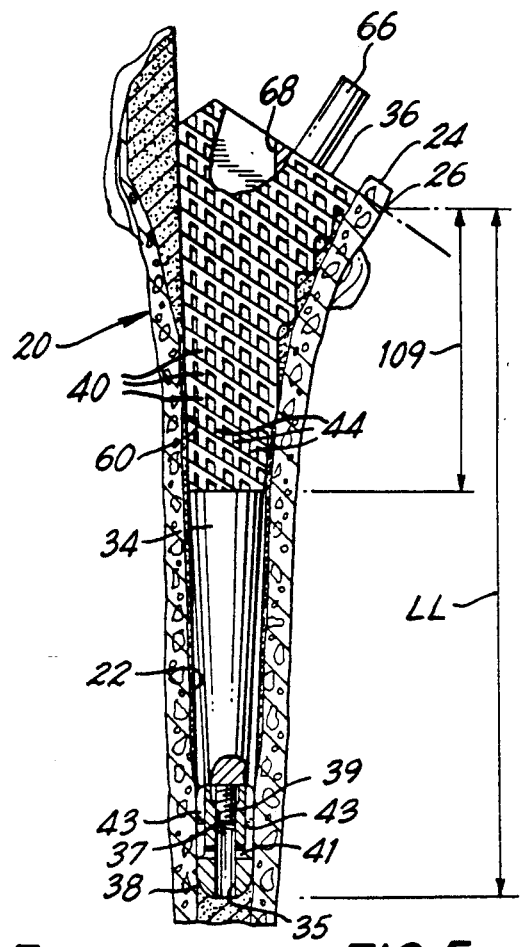
FIG. 1  FIG. 3  FIG. 5
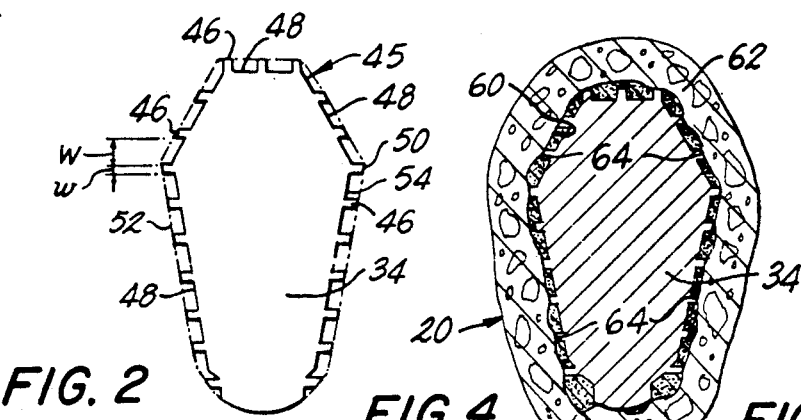
FIG. 2  FIG. 4  FIG. 1A

PROSTHETIC IMPLANT PROCEDURE AND FEMORAL BROACH THEREFOR

The present invention relates generally to the implant of prosthetic devices and pertains, more specifically, to the implant of a femoral stem, and a femoral broach utilized in the procedure.

The use of prosthetic implants to replace the natural joints of the body, either as a result of disease or injury to the natural joint, is becoming more and more commonplace. For example, in the replacement of a hip joint, it is very often necessary to replace the natural femoral head with a prosthetic stem which enters the femur and provides an accurately located and securely held prosthetic head in place of the natural femoral head. The procedures for implanting a prosthetic stem include the use of a broach or rasp, usually as the last step in preparing the femoral shaft for the reception of the prosthetic stem. The purpose of the broach or rasp is to provide precise contouring of the wall of the femoral shaft to the gross geometry of the prosthetic stem, thereby assuring accurate location and precise fit. The configuration of the broach or rasp is made to emulate that of the prosthetic stem to enable the attainment of the desired precision.

As suggested in co-pending application Ser. No. 083,483, entitled SURGICAL INSTRUMENT HANDLE COUPLING, filed Aug. 10, 1987, now U.S. Pat. No. 4,765,328, and owned by the assignee hereof, the broach itself may be used as a gauge of the accuracy of the broached cavity in the femur and can also be employed for the placement of a trial femoral neck and head for gauging the position of the actual prosthetic femoral head upon completion of the implant. The present invention provides a broach construction and a procedure which enables the broach to serve as a true gauge of the position which will be taken by the actual femoral stem upon completion of the implant and facilitates fixation of the femoral stem when seated at the proper position within the femur and attains several objectives and affords several advantages, some of which may be summarized as follows: Accuracy and precision in the location and fixation of a femoral stem within a femur, with simplified procedures; location of the broach within the femur in a precise position corresponding to the position which will be taken by the actual femoral stem so that the broach provides a true gauge of the position of the femoral stem after implant; provides a tactile feedback to the surgeon so that the surgeon actually can feel when the broach arrives at the appropriate position within the femoral cavity and contouring of the cavity for the reception of the femoral stem is complete; locates a post and a reference surface for completion of the preparation of the femur for the reception of the femoral stem to be implanted; provides for the placement of a trial femoral neck and head prior to implant of the actual femoral stem; provides improved fixation of the implanted femoral stem, utilizing either an interference fit or cement fixation; and reduces the time required for accurate placement of a femoral stem within the femur, thereby facilitating the entire implant procedure.

The above objects and advantages, as well as further objects and advantages, are attained by the present invention which may be described briefly as a procedure and a femoral broach for contouring the wall of a femoral cavity in a femur for the reception of a femoral stem to be seated within the femoral cavity in proper position relative to the femur, the femoral stem having an outer surface configuration which will be essentially contiguous with the wall of the femoral cavity upon seating of the femoral stem in proper position in the cavity, the femoral broach comprising: a blade having a proximal end, a distal end and an outer surface portion extending peripherally around the blade and longitudinally along the blade between the proximal end and the distal end; cutting teeth on the blade, the cutting teeth being aligned along longitudinal rows of teeth spaced apart along the periphery of the blade such that the longitudinal rows of teeth establish an outer profile configuration which includes a multiplicity of alternating longitudinal ribs and grooves generally parallel to one another and spaced apart peripherally along the outer surface portion of the blade, with the longitudinal ribs including apices lying along an outer envelope defined by the apices, the longitudinal ribs occupying a sufficient part of the periphery of the outer surface portion and being placed sufficiently closely adjacent one another so that the outer envelope defined by the apices of the ribs has a configuration which emulates the outer surface configuration of the femoral stem for the subsequent establishment of a seating surface in the femoral cavity for the femoral stem, which seating surface will be at least partially contiguous with harder portions of the bone of the femur, such that upon longitudinal movement of the blade into the femoral cavity, the wall of the cavity will be contoured by the cutting teeth and provided with grooves and ribs complementary to the corresponding ribs and grooves along the outer surface portion of the blade, with the grooves of the contoured femoral cavity having roots lying along an inner envelope corresponding to the outer envelope of the blade and emulating the outer surface configuration of the femoral stem for providing the seating surface, the inner envelope being at least partially contiguous with the harder portions of the bone of the femur while the ribs in the wall of the cavity provide softer portions of the bone of the femur which extend into the inner envelope for compression between the femoral stem and the femur when the femoral stem subsequently is seated upon the seating surface within the cavity, in proper position relative to the femur. The femur is provided with a passage into which the blade may be guided more precisely by a proximal tip complementary to the passage, and the proximal tip may be removed and replaced selectively at the proximal end of the blade for the selection of a proximal tip of appropriate dimensions. Preferably, the proximal tip includes vent conduits which provide open communication between the distal end of the blade and the passage, through the distal tip toward the proximal end of the blade, for facilitating advancement and retraction of the blade within the passage.

The invention will be understood more fully, while still further objects and advantages will become apparent, in the following detailed description of a preferred embodiment of the invention illustrated in the accompanying drawing, in which:

FIG. 1 is a somewhat diagrammatic elevational view, partially sectioned, showing a broach of the present invention about to be inserted into a partially prepared femur in accordance with the procedure of the invention;

FIG. 1A is an enlarged fragmentary exploded view, partially sectioned, of the distal end and the distal tip of the broach;

FIG. 2 is an enlarged cross-sectional view taken along line 2—2 of FIG. 1;

FIG. 3 is a view similar to FIG. 1, but with the broach in place within the femur;

FIG. 4 is an enlarged cross-sectional view taken along line 4—4 of FIG. 3;

FIG. 5 is an enlarged fragment of FIG. 3, with a component part removed;

Figure 6:
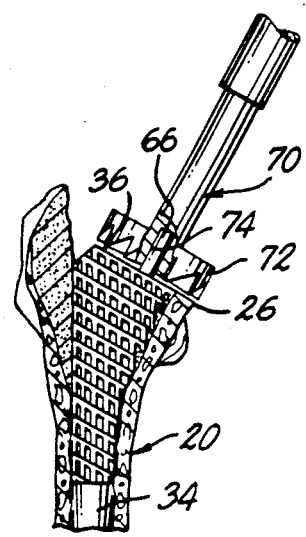
FIG. 6 is a fragmentary view of a portion of FIG. 5, reduced in size, and illustrating a further operation.

Referring now to the drawing, and especially to FIG. 1 thereof, the proximal portion of a femur 20 has been subjected to an initial neck resection and has been provided with a passage 22 in partial preparation for the implant of a femoral stem in the femur. The initial resection level 24 is made slightly higher than the desired final resection level 26 to enable subsequent calcar planing, as will be explained hereinafter, for accuracy in the location of the final resection level 26 relative to the implanted femoral stem. Passage 22 has been formed initially by the insertion of progressively larger reamers (not shown) into the canal 28 of the femur 20. A broach 30 includes a handle 32 and a blade 34 affixed to the handle 32 for selective detachment, as explained in detail in the aforesaid patent application Ser. No. 083,483. Suffice it to say at this juncture that any one of a series of blades 34 may be selected and attached to handle 32 for accomplishing the broaching of passage 22 to establish a cavity for the reception of a femoral stem. Initial broaching ordinarily is accomplished with a broach having a blade somewhat smaller than the blade which will broach the final contour of the cavity which will receive the femoral stem, and progressively larger blades are employed until the final blade 34 is attached to handle 32. For purposes of illustration, only the final broaching step is shown herein, with the final blade 34 shown in place upon handle 32.

Blade 34 has an overall configuration somewhat similar to the femoral stem which will be implanted within the femur 20 and includes a proximal surface 36 at the proximal end of the blade 34 and a distal tip 38 at the distal end of the blade 34. During advancement of the blade 34 into the passage 22, distal tip 38 serves as a guide which pilots the blade 34 within passage 22 to assure proper relative positioning of the blade 34 and the femur 20. Distal tip 38 is interchangeable to permit the selection of different diameters in order to match the diameter of passage 22 for a precision fit. Thus, as best seen in FIG. 1A, distal tip 38 includes an axial bore 35 which is threaded at 37 for selective threading onto and off of a corresponding threaded stud 39 at the distal end of the blade 34 so as to be selectively interchangeable (also see FIG. 5). Vent means, in the form of a vent conduit 41 and vent channels 43 communicating with bore 35, establish open communication between the distal end of blade 34 and the portion of the passage 22 above the distal tip 38, that is, in the direction from the distal end of the blade 34 toward the proximal end of the blade 34, to assure that distal tip 38 will not unduly impede longitudinal movement within passage 22, during advancement and retraction of the blade 34, despite the close fit between the distal tip 38 and passage 22, upon insertion and withdrawal of the blade 34, thereby enabling a precise fit between distal tip 38 and passage 22 and assuring precision in the location of the femoral stem to be implanted in the femur 20.

A relatively large number of cutting teeth 40 are integral with the blade 34 along an outer surface portion 42 of the blade 34 and are aligned in rows 44 which follow lines extending longitudinally along the outer surface 42 between the proximal surface 36 and the distal tip 38. Rows 44 are parallel with one another and establish a cross-sectional outer profile configuration 45 which includes a multiplicity of parallel alternating ribs 46 and grooves 48, as illustrated in FIG. 2, extending longitudinally along and spaced apart peripherally about the outer surface 42 of the blade 34. The ribs 46 include apices 50 which lie along an outer envelope 52 defined by the apices 50, and the grooves 48 each have a root 54. The ribs 46 are sufficient in number and in width to assure that the envelope 52 is well-defined and emulates the cross-sectional configuration of the corresponding outer surface configuration of the femoral stem which is to be implanted in the femur 20. Thus, for each rib 46 and an adjacent groove 48, approximately twenty-five percent of the cross-sectional profile configuration is taken up with the rib 46, while the remaining approximately seventy-five percent of the profile configuration is taken up by the adjacent groove 48. Stated in other terms, the preferred ratio between the width w of a rib 46 and the width W of an adjacent groove 48 is approximately 1:4. The height of each rib 46, that is, the distance between an apex 50 and a corresponding root 54, preferably is the measure of one size difference between consecutive femoral stem sizes, and the corresponding broach sizes. The difference usually is one millimeter. The preferred peripheral spacing between adjacent ribs 46 (the width W) is about two to three millimeters. The outer surface portion 42 of the blade 34 extends longitudinally from the proximal surface 36 toward the distal tip 38 and preferably covers about forty percent of the total length L of the blade 34 from the proximal surface 36 to the distal tip 38.

As best seen in FIGS. 3 and 4, when the blade 34 of broach 30 is advanced fully into the passage 22 to complete a cavity 60 having a contour configuration appropriate for the reception of the femoral stem to be implanted in the femur, at least some of the ribs 46 seat against the harder bone of the femur 20, namely, either against highly densified cancellous or cortical bone 62, as illustrated at locations 64, thereby placing the blade 34 in precisely the position to be occupied subsequently by the femoral stem. The attainment of this seated position of the blade 34 is transmitted to the surgeon by the feel of the blade 34 bottoming on the harder bone 62, thereby providing the surgeon with a positive tactile determination of the correct position of the blade 34 and the concomitant completion of the contouring procedure. The handle 32 then is detached from the blade, in the manner described fully in the aforesaid U.S. Pat. No. 4,765,328, exposing the proximal surface 36, a post 66 projecting from the proximal surface 36 and a recess 68 extending into the blade 34 at the proximal surface 36, as shown in FIG. 5.

In the illustrated example, the proximal surface 36 is located below the initial resection level 24 and planing of the calcar will be necessary to establish the final resection level 26, which is flush with the proximal surface 36. Turning now to FIG. 6, a rotary calcar plane 70 has a rotating cutter 72 and a locator bore 74 located along the axis of rotation of the cutter 72. The diameter of the locator bore 74 is complementary to the diameter of the cylindrical post 66 so that the calcar plane 70 is located and guided by the placement of the locator bore 74 over the post 66. The cutter 72 is advanced along the post 66 until the proximal surface 36 is reached and the calcar is planed to the point where the final resection level 26 is established. The calcar plane 72 then is removed, once more exposing the post 66 for the next step of the procedure.

Figure 7:
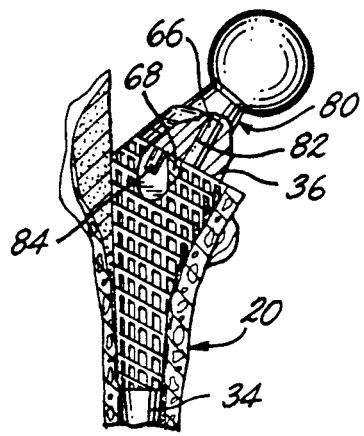
FIG. 7 is a fragmentary view similar to FIG. 6, but with a trial femoral neck and head in place.

As seen in FIG. 7, a trial femoral neck and head 80 now may be placed on the blade 34 to gauge the location of the femoral neck and head of the completed implant. Thus, the trial femoral head and neck 80 includes a locator hole 82 complementary to the post 66 and a locator pin 84 engageable with the recess 68 in the blade 34 so that the trial neck and head 80 readily is placed in proper position on the blade 34 to emulate the complete femoral component to be implanted in the femur 20. Upon completion of the trial, the trial neck and head 80 is removed, the handle 32 again is attached to the blade 34 and the blade 34 is withdrawn from the contoured cavity 60.

Figure 8:
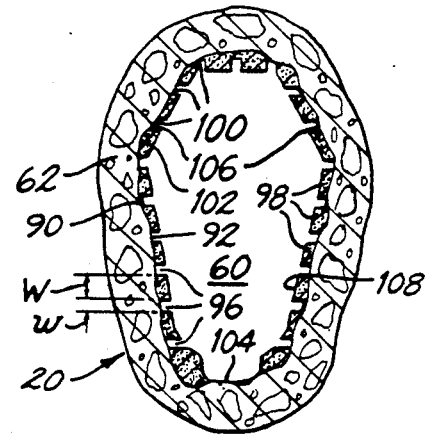
FIG. 8 is a cross-sectional view similar to FIG. 4, but with the broach removed.

Turning now to FIG. 8, withdrawal of the blade 34 from the cavity 60 leaves behind a contoured configuration 90 in the wall 92 of the cavity 60, which contoured configuration 90 includes grooves 96, complementary to the ribs 46 of the outer profile configuration 45, and ribs 98, complementary to the grooves 48 of the outer profile configuration 45. The grooves 96 include roots 100 lying along an inner envelope 102 defined by the roots 100 of the grooves 96, the inner envelope 102 of the cavity 60 corresponding to the outer envelope 52 of the blade 34 and emulating the outer surface configuration of the femoral stem to be implanted so as to provide a seating surface 104 for the femoral stem, which seating surface 104 is at least partially contiguous with the harder bone 62 of the femur, as illustrated at locations 106. The ribs 98 are comprised of cancellous bone, which is the softer bone of the femur 20, and extend into the inner envelope 102 established by the roots 100 of the grooves 96. As described above, the preferred ratio between the width w of a groove 96 and the width W of an adjacent rib 98 is about 1:4. Likewise, the height of each rib 98, that is, the distance between an apex 108 of a rib 98 and the root 100 of an adjacent groove 96, preferably is the measure of one size difference between consecutive femoral stem sizes. The difference usually is one millimeter. The preferred peripheral spacing between adjacent grooves 96 (the width W) is about two to three millimeters. The grooves 96 and ribs 98 preferably extend along only a proximal portion 109 of the cavity 60, which proximal portion 109 comprises approximately forty percent of the total longitudinal length LL of the cavity 60.

Figure 9:
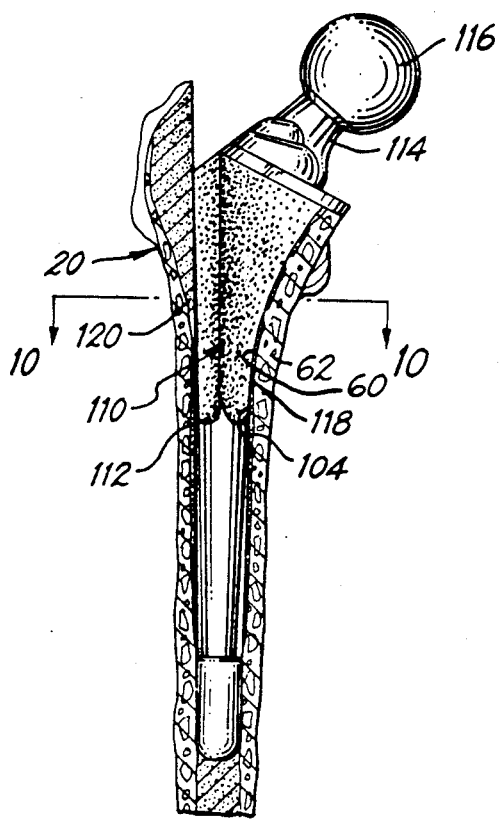
FIG. 9 is a view similar to FIG. 5, but illustrating an actual femoral stem in place within the femur.
Figure 10:
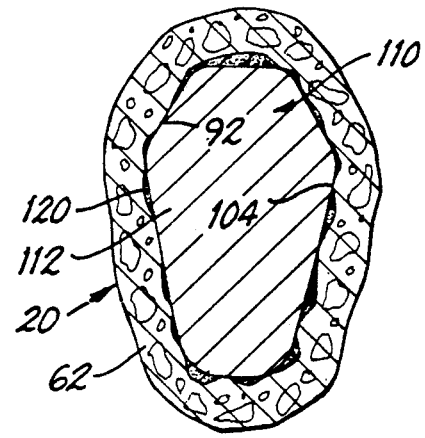
FIG. 10 is an enlarged cross-sectional view taken along line 10—10 of FIG. 9.

Referring now to FIGS. 9 and 10, the femoral component to be implanted is illustrated at 110 and is seen to include a femoral stem 112, a femoral neck 114 and a femoral head 116. The femoral stem 112 is inserted into the prepared contoured cavity 60 and is advanced until the outer surface 118 of the femoral stem 112 is seated upon the seating surface 104 provided in the cavity 60, thus assuring the location of the femoral component 110 in proper position relative to the femur 20. The softer bone, left behind in the form of ribs 98, is shown at 120 compressed between the femoral stem 112 and the harder bone 62 of the femur 20 by the insertion of the femoral stem 112 and establishes the desired interference fit which serves to affix the femoral component 110 within the femur 20. In those instances where the femoral component 110 is to be affixed with cement (not shown), the ribbed and grooved configuration of the contoured wall 92 of the femoral cavity 60 serves to enhance the interdigitation of the cement.

It is noted that the blade 34 of the broach 30 provides a true gauge of the ultimate position of the implanted femoral component 110 since the blade 34 bottoms on the harder bone of the prepared femoral cavity 60, against the seating surface 104 in the cavity 60, and thus occupies precisely the same position as will be occupied by the femoral component 110 after implant. In this manner, the blade 34 provides for accurate calcar planing to complete the preparation of the femur with increased ease and precision, and facilitates the conduct of trials prior to actual implant of the femoral component. Completion of the contouring of the wall 92 of the cavity 60 is signalled to the surgeon in a positive tactile manner, thereby facilitating precision with confidence.

It is to be understood that the above detailed description of a preferred embodiment of the invention is provided by way of example only. Various details of design and construction may be modified without departing from the true spirit and scope of the invention, as set forth in the appended claims.

The embodiments of the invention in which an exclusive property or privilege is claimed are defined as follows:

1. A femoral broach for advancement into a passage placed within a femur in preparation for the implant of a femoral stem to contour the wall of a femoral cavity in the femur for the reception of a femoral stem to be seated within the femoral cavity in proper position relative to the femur, the femoral stem having an outer surface configuration which will be essentially contiguous with the wall of the femoral cavity upon seating of the femoral stem in proper position in the cavity, the femoral broach comprising:

a blade having a proximal end, a distal end and an outer surface portion extending peripherally around the blade and longitudinally along the blade between the proximal end and the distal end;

cutting teeth on the blade, the cutting teeth being aligned along longitudinal rows of teeth spaced apart along the periphery of the blade such that the longitudinal rows of teeth establish an outer profile configuration which includes a multiplicity of alternating longitudinal ribs and grooves generally parallel to one another and spaced apart peripherally along the outer surface portion :of the blade, with the longitudinal ribs including apices lying along an outer envelope defined by said apices, the longitudinal ribs occupying a sufficient part of the periphery of the outer surface portion and being placed sufficiently closely adjacent one another so that the outer envelope defined by the apices of the ribs has a configuration which emulates the outer surface configuration of the femoral stem for the subsequent establishment of a seating surface in the femoral cavity for the femoral stem, which seating surface will be at least partially contiguous with harder portions of the bone of the femur, such that upon longitudinal movement of the blade into the femoral cavity, the wall of the cavity will be cut by the cutting teeth to be contoured provided with grooves and ribs complementary to the corresponding ribs and grooves along the outer surface portion of the blade, with the grooves of the contoured femoral cavity having roots lying along an inner envelope corresponding to the outer envelope of the blade and emulating the outer surface configuration of the femoral stem for providing said seating surface, the inner envelope being at least partially contiguous with the harder portions of the bone of the femur while the ribs in the wall of the cavity provide softer portions of the bone of the femur which extend into the inner envelope for compression between the femoral stem and the harder portions of the bone of the femur when the femoral stem subsequently is seated upon said seating surface within the cavity, in proper position relative to the femur.

2. The invention of claim 1 wherein each rib of the outer profile configuration has a peripheral width less than the peripheral width of an adjacent groove of the outer profile configuration.

3. The invention of claim 2 wherein the ratio of the width of each rib of the outer profile configuration and the width of the adjacent groove of the outer profile configuration is approximately 1:4.

4. The invention of claim 1 wherein each groove of the outer profile configuration has a root and the height of the adjacent rib, between the root of the groove and the apex of the rib, is approximately one millimeter.

5. The invention of claim 1 wherein the peripheral spacing between adjacent ribs of the outer profile is approximately two to three millimeters.

6. The invention of claim 1 wherein the outer surface portion extends longitudinally from the proximal end toward the distal end for a portion of the length of the blade.

7. The invention of claim 6 wherein said portion of the length of the blade comprises approximately forty percent of the length of the blade.

8. The invention of claim 1 including means for locating a trial femoral neck and head at the proximal end of the blade.

9. The invention of claim 1 including:
a distal tip for placement at the distal end of the blade to enable guiding of the blade within the passage by the distal tip during advancement of the blade into the passage; and
securement means enabling selective removal and replacement of the distal tip at the distal end of the blade for selection of a distal tip complementary to the passage for precise guiding, and securement of the selected distal tip at the distal end of the blade.

10. The invention of claim 9 wherein the distal tip includes vent means providing open communication between the distal end of the blade and the passage, through the distal tip toward the proximal end of the blade, for facilitating advancement and retraction of the blade within the passage.

11. The invention of claim 1 including:
a distal tip at the distal end of the blade, the distal tip being complementary with the passage for precise guiding of the blade within the passage during advancement of the blade into the passage; and
vent means providing open communication between the distal end of the blade and the passage, through the distal tip toward the proximal end of the blade for facilitating advancement and retraction of the blade within the passage.

12. In a procedure for contouring the wall of a femoral cavity extending longitudinally within the femur for the reception of a femoral stem to be seated within the femoral cavity in proper position relative to the femur, the femoral stem having an outer surface configuration which will be essentially contiguous with the wall of the femoral cavity upon seating of the femoral stem in proper position in the cavity, the improvement comprising: providing the wall of the femoral cavity with a multiplicity of alternating longitudinal grooves and ribs generally parallel to one another and spaced apart peripherally along the wall of the cavity, the grooves of the contoured femoral cavity having roots lying along an inner envelope defined by the roots of the grooves, the longitudinal grooves occupying a sufficient part of the periphery of the wall of the cavity and being placed sufficiently closely adjacent one another so that the inner envelope defined by the roots of the grooves has a configuration which emulates the outer surface configuration of the femoral stem for providing a seating surface for the femoral stem, the inner envelope being at least partially contiguous with harder portions of the bone of the femur while the ribs in the wall of the cavity provide softer portions of the bone of the femur which extend into the inner envelope for compression between the femoral stem and the harder portion of the bone of the femur when the femoral stem subsequently is seated upon said seating surface within the cavity, in proper position relative to the femur.

13. The invention of claim 12 wherein each groove in the wall of the cavity has a peripheral width less than the peripheral width of an adjacent rib.

14. The invention of claim 13 wherein the ratio of the width of each groove and the width of the adjacent rib is approximately 1:4.

15. The invention of claim 12 wherein each rib on the wall of the cavity has an apex, and the height of the rib, between the root of the adjacent groove and the apex of the rib, is approximately one millimeter.

16. The invention of claim 12 wherein the peripheral spacing between adjacent grooves is approximately two to three millimeters.

17. The invention of claim 12 wherein the longitudinal grooves and ribs extend along only a proximal portion of the cavity.

18. The invention of claim 17 wherein the proximal portion of the cavity comprises approximately forty percent of the longitudinal length of the cavity.

19. A femoral broach for advancement into a passage placed within a femur in preparation for the implant of a femoral stem to contour the wall of a femoral cavity in the femur for the reception of the femoral stem so that the femoral stem will be seated within the femoral cavity in proper position relative to the femur, the femoral stem having an outer surface configuration which will be essentially contiguous with the wall of the femoral cavity upon seating of the femoral stem in proper position in the cavity, the femoral broach comprising:
a blade having a proximal end, a distal end and an outer surface portion extending peripherally around the blade and longitudinally along the blade between the proximal end and the distal end;

a distal tip for placement at the distal end of the blade, the distal tip being complementary with the passage for precise guiding of the blade within the passage during advancement of the blade into the passage; and securement means enabling selective removal and replacement of the distal tip at the distal end of the blade for selection of a distal tip complementary to the passage, and securement of the selected distal tip at the distal end of the blade.

20. The invention of claim 19 wherein the distal tip includes vent means providing open communication between the distal end of the blade and the passage, through the distal tip toward the proximal end of the blade, for facilitating advancement and retraction of the blade within the passage.

21. A femoral broach for advancement into a passage placed within a femur in preparation for the implant of a femoral stem to contour the wall of a femoral cavity in the femur for the reception of the femoral stem so that the femoral stem will be seated within the femoral cavity in proper position relative to the femur, the femoral stem having an outer surface configuration which will be essentially contiguous with the wall of the femoral cavity upon seating of the femoral stem in proper position in the cavity, the femoral broach comprising:

a blade having a proximal end, a distal end and an outer surface portion extending peripherally around the blade and longitudinally along the blade between the proximal end and the distal end;

a distal tip at the distal end of the blade, the distal tip being complementary with the passage for precise guiding of the blade within the passage during advancement of the blade into the passage; and vent means providing open communication between the distal end of the blade and the passage, through the distal tip toward the proximal end of the blade, for facilitating advancement and retraction of the blade within the passage.

* * * * *